United States Patent
Daniel et al.

(10) Patent No.: US 11,648,017 B2
(45) Date of Patent: May 16, 2023

(54) DRILL GUIDE WITH INTEGRATED VARIABLE ANGLE AND ZERO DEGREE DRILLING

(71) Applicant: DEPUY SYNTHES PRODUCTS, INC., Raynham, MA (US)

(72) Inventors: Steffan Daniel, Zuchwil (CH); Mirko Rocci, Bettlach (CH); This Aebi, Grenchen (CH); Johanna F. Menze, Zuchwil (CH); Joel Oberli, Basel-Landschaft (CH)

(73) Assignee: DePuy Synthes Products, Inc., Raynham, MA (US)

( * ) Notice: Subject to any disclaimer, the term of this patent is extended or adjusted under 35 U.S.C. 154(b) by 321 days.

(21) Appl. No.: 17/011,425

(22) Filed: Sep. 3, 2020

(65) Prior Publication Data
US 2022/0061860 A1 Mar. 3, 2022

(51) Int. Cl.
*A61B 17/17* (2006.01)
*A61B 17/00* (2006.01)

(52) U.S. Cl.
CPC .. *A61B 17/1728* (2013.01); *A61B 2017/0042* (2013.01); *A61B 2017/00738* (2013.01)

(58) Field of Classification Search
CPC combination set(s) only.
See application file for complete search history.

(56) References Cited

U.S. PATENT DOCUMENTS

| | | | |
|---|---|---|---|
| 7,883,513 B2 | 2/2011 | Ralph et al. | |
| 2003/0083667 A1 | 5/2003 | Ralph et al. | |
| 2005/0038444 A1 | 2/2005 | Binder et al. | |
| 2009/0204157 A1 | 8/2009 | Fernandez Dell 'Oca | |
| 2010/0130983 A1* | 5/2010 | Thornhill | A61B 17/1728 606/96 |
| 2013/0012945 A1 | 1/2013 | Chreene et al. | |
| 2018/0353301 A1 | 12/2018 | Goldstein et al. | |

FOREIGN PATENT DOCUMENTS

| | | |
|---|---|---|
| CN | 104905846 B | 6/2017 |
| DE | 102011079562 B4 | 3/2018 |
| WO | 2008/064211 A1 | 5/2008 |

* cited by examiner

*Primary Examiner* — Sameh R Boles
(74) *Attorney, Agent, or Firm* — Kramer & Amado, P.C.

(57) ABSTRACT

A drill guide, including: frustoconical body with a first opening at a narrower distal end and second opening at a wider the proximal end; a first support with a first end connected to the frustoconical body and a second end; a zero angle guide with an opening aligned with the first opening and wherein the zero angle guide is connected to the second end of the first support.

8 Claims, 9 Drawing Sheets

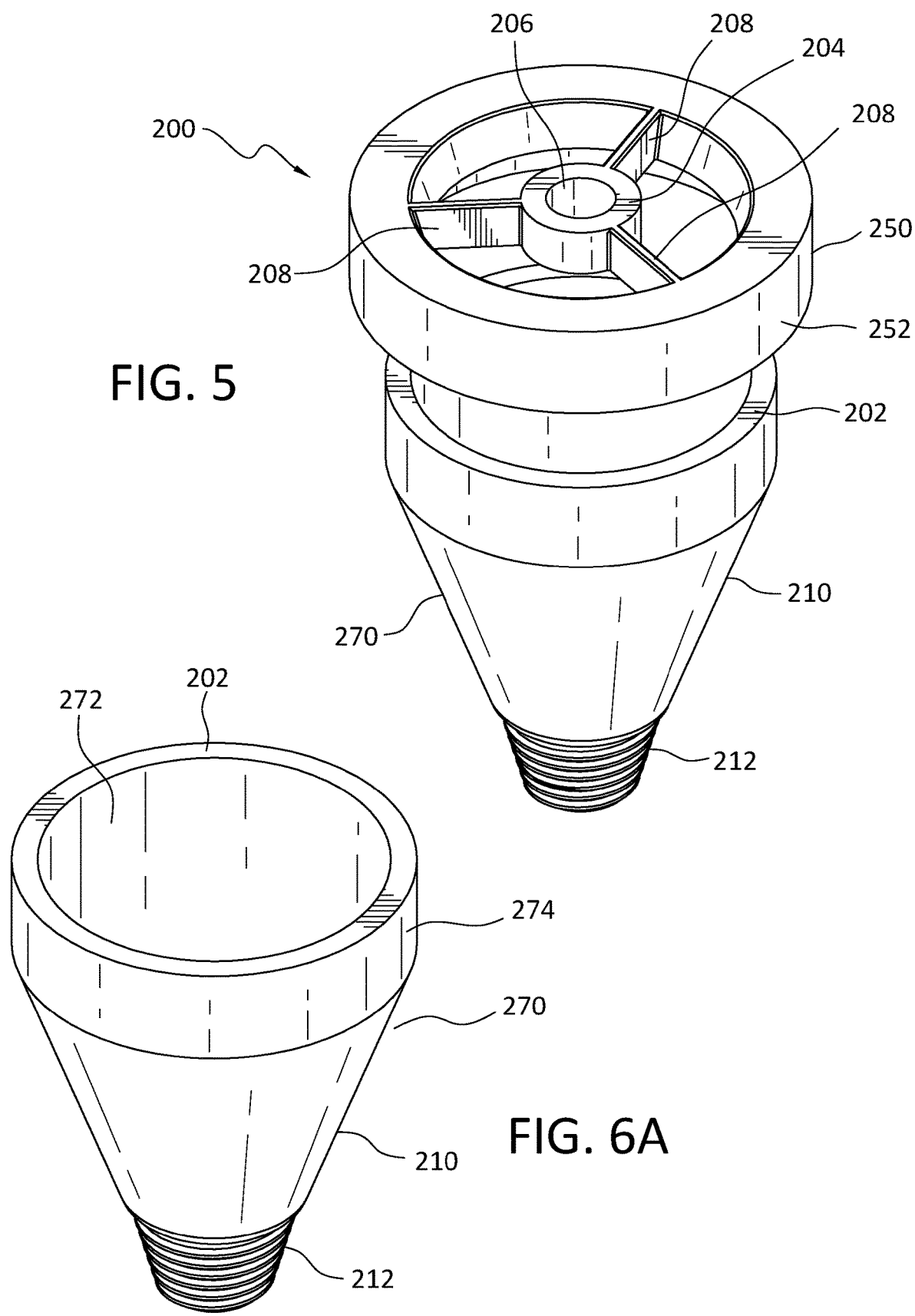

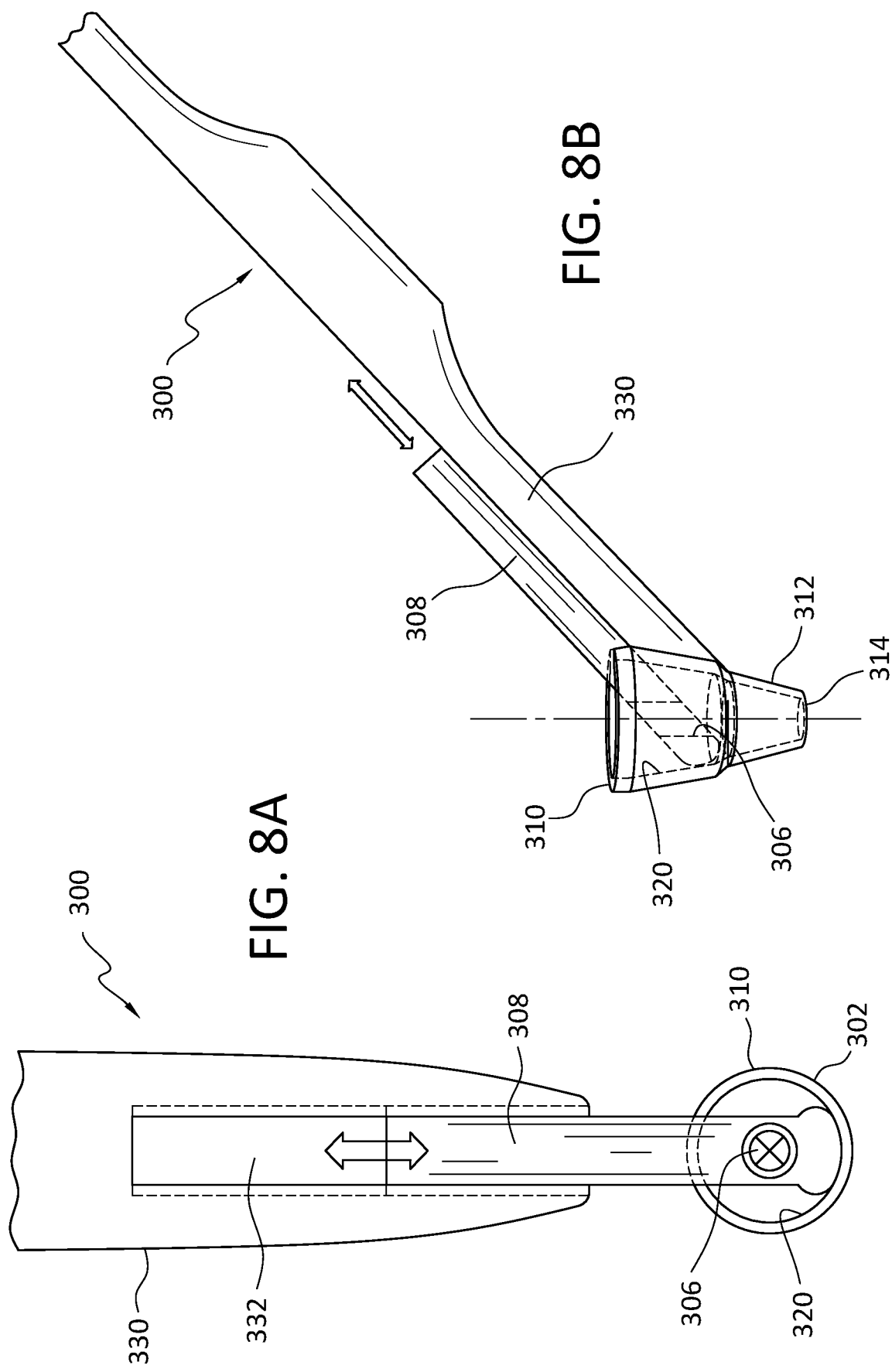

DRILL GUIDE WITH INTEGRATED VARIABLE ANGLE AND ZERO DEGREE DRILLING

TECHNICAL FIELD

Various exemplary embodiments disclosed herein relate generally to a drill guide with integrated variable angle and zero degree drilling.

BACKGROUND

Bone plates are widely used to secure bone fractures. Such bone plates include a number of holes, and screws are inserted through the holes into the bone and/or bone fragments to be repaired. Typically a surgeon will use a drill guide to accurately drill holes in the bone to receive the screws used to secure the bone plate to the bone. The drill guide ensures that a hole drilled in the bone is perpendicular to the bone or axially aligned with the screw hole in the bone plate or at some other desired angle. Variable angle (VA) locking screws have been developed that allow for the insertion of the screw that secures the bone plate at various angles.

Variable angle locking screws provide the ability to create a fixed-angle construct while also allowing the surgeon the freedom to choose the screw trajectory. A fixed-angle construct provides advantages in osteopenic bone or multifragmentary fractions. With variable angle (VA) screw technology, screw angulation is unlimited with a specified cone angle around the central axis of the bone plate hole. VA screws enable optimal screw positioning and offers many benefits by allowing the surgeon to: target fragments with high-quality bone, especially in patients with osteopenic bone; adjust screw direction after bending the plate; position screws precisely to avoid joint penetration; redirect screw position to avoid existing implants, prostheses, or independent lag screws; and adapts screw position to accommodate varied patient anatomy and capture fracture fragments.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a drill guide, including: frustoconical body with a first opening at a narrower distal end and second opening at a wider the proximal end; a first support with a first end connected to the frustoconical body and a second end; a zero angle guide with an opening aligned with the first opening and wherein the zero angle guide is connected to the second end of the first support.

Various embodiments are described, wherein the frustoconical body includes threads at the distal end configured to engage a screw hole in a bone plate.

Various embodiments are described, wherein the distal end of frustoconical body has a shape configured to engage a screw hole in a bone plate, wherein the shape of the distal end is complementary to the shape of the screw hole.

Various embodiments are described, further including a second support with a first end connected to the frustoconical body and a second end connected to the zero angle guide.

Various embodiments are described, wherein the zero angle guide is adjacent the distal end of the frustoconical body.

Various embodiments are described, further including a handle.

Various embodiments are described, wherein the handle is connected to and extends from the zero angle guide along a central axis of the zero angle hole and wherein the handle has a central opening aligned with the zero angle guide opening.

Various embodiments are described, wherein the handle is connected to and extends from the frustoconical body.

Further various embodiments relate to a drill guide, including: guide body with a frustoconical shape with a first opening at a narrower distal end and second opening at a wider the proximal end; a guide assembly including: a circular body; a first support with a first end connected to the circular body and a second end; a zero angle guide with an opening wherein the zero angle guide is connected to the second end of the first support, wherein the guide assembly is configured to engage the proximal end of the guide body so that the zero angle guide opening is aligned with the first opening.

Various embodiments are described, wherein the guide body includes threads at the distal end configured to engage a screw hole in a bone plate.

Various embodiments are described, wherein the distal end of guide body has a shape configured to engage a screw hole in a bone plate, wherein the shape of the distal end is complementary to the shape of the screw hole.

Various embodiments are described, wherein the guide assembly further includes a second support with a first end connected to the circular body and a second end connected to the zero angle guide.

Various embodiments are described, further including a handle connected to and extending from the guide body.

Various embodiments are described, wherein guide body includes a lip at the proximal end configured to engage the guide assembly.

Various embodiments are described, wherein the circular body further includes a circular ledge configured to engage the proximal end of the guide body.

Various embodiments are described, the circular body includes a frustoconical shaped inner surface, wherein the inner surface connects to the support and wherein the inner surface substantially aligns with an inner surface of the guide body.

Further various embodiments relate to a drill guide, including: a variable angle (VA) guiding cone with a first opening at a narrower distal end and second opening at a wider proximal end and an aperture in a side of the VA guiding cone; a handle connected to the VA guiding cone with a sliding groove; and a sliding bar slidably attached to the sliding groove wherein the sliding bar has a drill opening at a distal end, wherein the sliding bar is configured to slide along the sliding groove such that the distal end of the sliding bar enters an interior of the VA guiding cone through the aperture and the drill opening is aligned with the first opening.

Various embodiments are described, wherein the VA guiding cone includes threads at the distal end configured to engage a screw hole in a bone plate Various embodiments are described, wherein the distal end of guiding cone has a shape configured to engage a screw hole in a bone plate, wherein the shape of the distal end is complementary to the shape of the screw hole Various embodiments are described, wherein the aperture is between the handle and proximal end of the VA guide cone.

Various embodiments are described, wherein the aperture is between the handle and distal end of the VA guide cone.

BRIEF DESCRIPTION OF THE DRAWINGS

In order to better understand various exemplary embodiments, reference is made to the accompanying drawings, wherein:

FIG. 5 illustrates another embodiment of a drill guide with a separate guide assembly;

FIGS. 6A and 6B illustrate perspective and cross-sectional views, respectively, of the guide body;

FIGS. 8A and 8B illustrate another embodiment of a drill guide.

To facilitate understanding, identical reference numerals have been used to designate elements having substantially the same or similar structure and/or substantially the same or similar function.

DETAILED DESCRIPTION

Figure 1A:
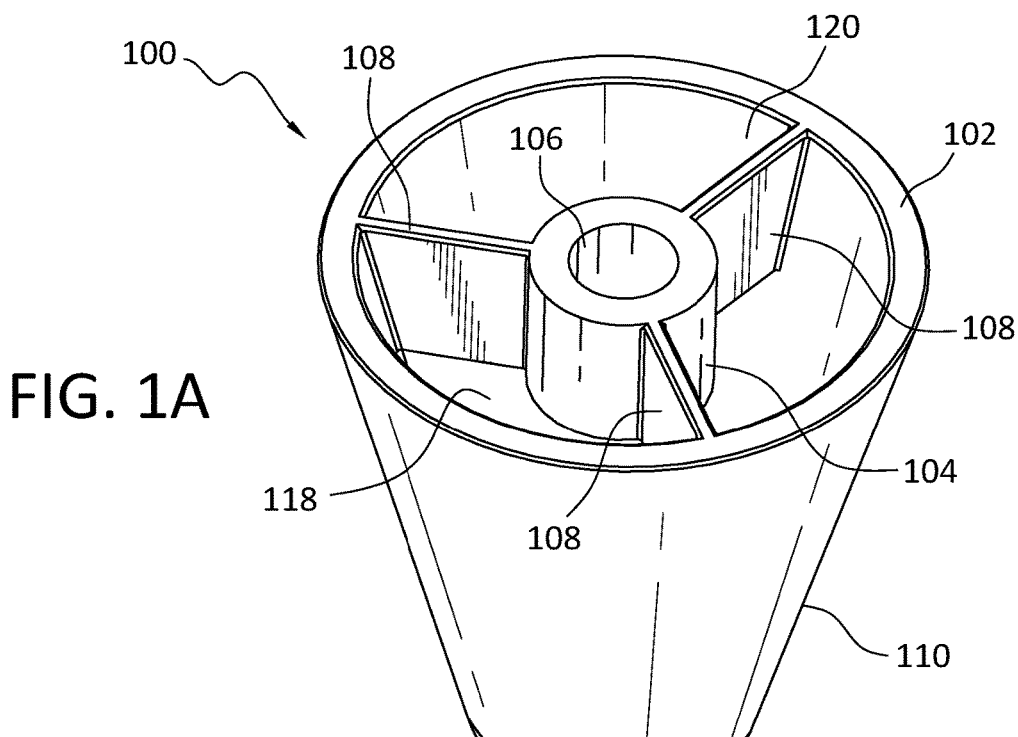
FIGS. 1A-D illustrate top perspective, bottom perspective, side, and cross-sectional views, respectively, of an embodiment of a drill guide that includes zero degree and VA drilling.
Figure 1B:
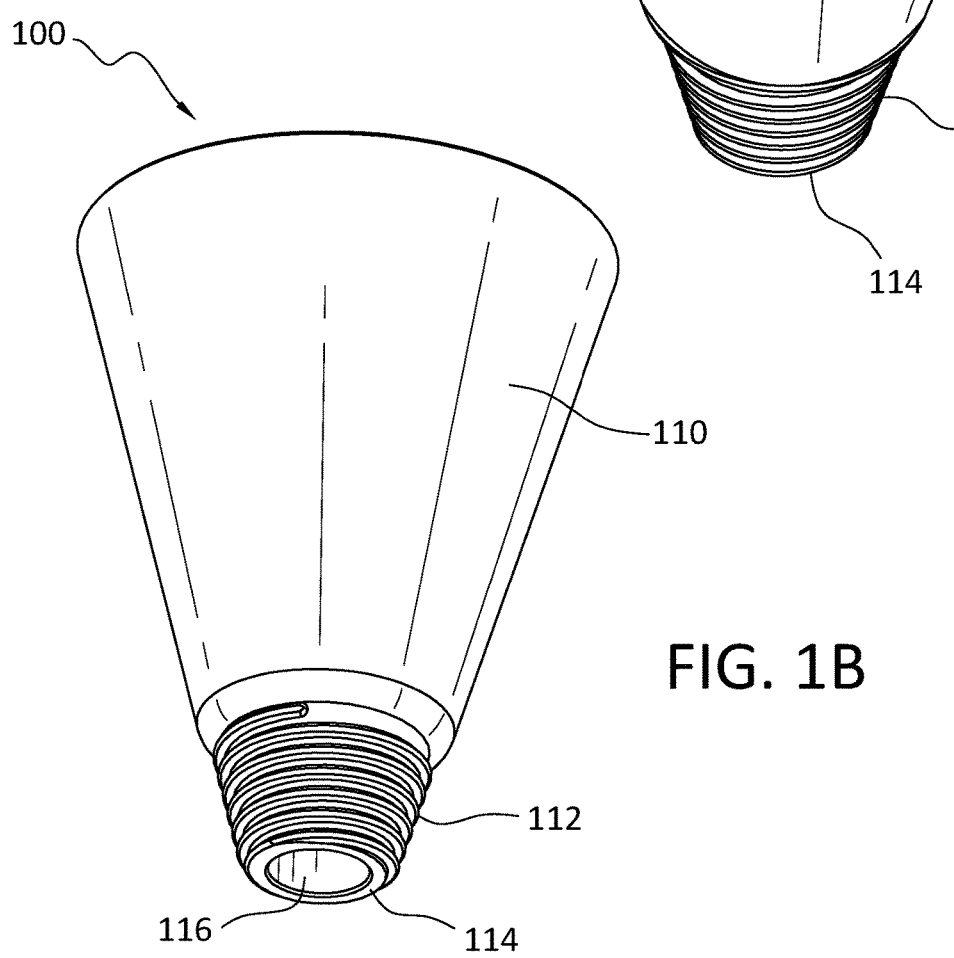
Figure 1C:
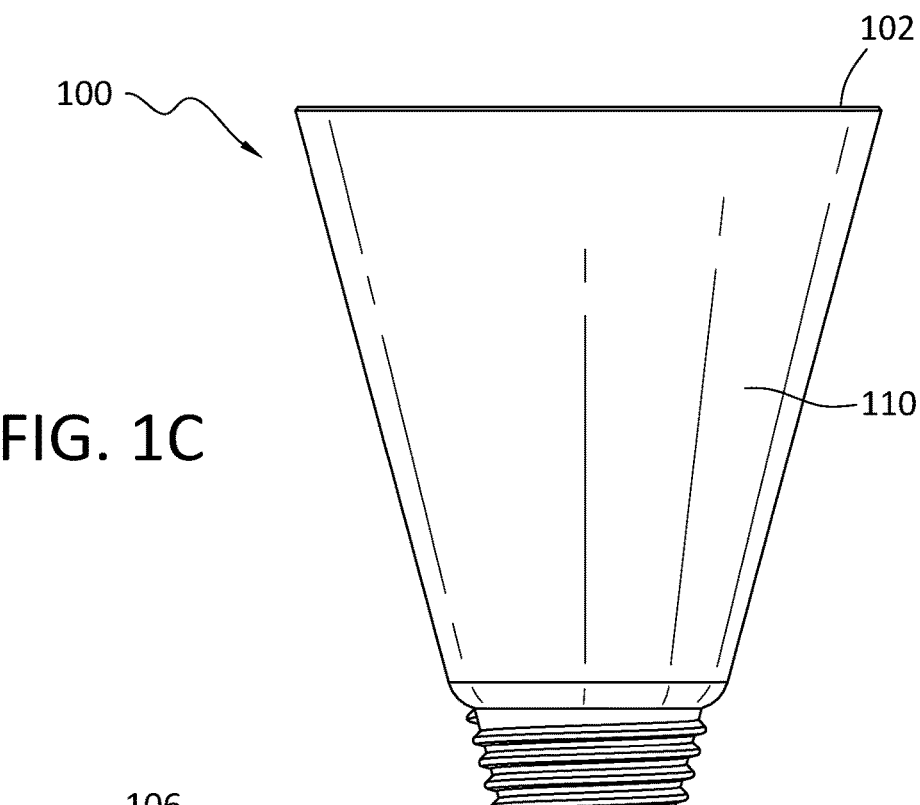

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

When VA screws are used, a drill guide may be used to limit the angle of hole drilled in the bone. At the same time, in some situations it is desired that the VA or other screws are inserted with a zero angle. A zero angle hole includes a hole that substantially aligns with the axis of the bone plate screw hole or that is substantially perpendicular to a surface of the bone to be drilled. A drill guide may be used to accommodate the precise drilling of such a hole. Accordingly, there is a need for a drill guide that provides the surgeon the options of drilling a zero angle (i.e., drilling coaxially with the axis of the hole) hole or a hole at an angle off the axis of the hole that is within an angle limit. Such a device will replace the need for two different drill guides, i.e., one for zero angle holes and one that limits the angle of holes to a desired angular limit.

FIGS. 1A-D illustrate top perspective, bottom perspective, side, and cross-sectional views, respectively, of an embodiment of a drill guide that includes zero degree and VA drilling. The drill guide 100 is generally of a frustoconical shape as shown by an frustoconical wall defined by outer surface 110 and inner surface 120. The drill guide 100 includes a proximal end with a proximal edge 102 and a distal end with a distal edge 114. The distal end is configured to engage a screw hole on the bone plate. This may be facilitated by a thread 112 on the outer surface 110. The thread 112 may engage threads in the bone plate hole. This will ensure that the drill guide 110 is securely engaged with the bone plate while screw holes are drilled in the bone. The thread 112 also helps to ensure that the drill guide 100 is substantially aligned with the axis of the bone plate screw hole to provide the surgeon confidence in the angle of the hole being drilled into the bone. In other embodiments the distal end of the drill guide 100 may be shaped to fit securely in the bone plate screw hole in a specific desired orientation because of the complementary mating surfaces. Such an approach would save time because the drill guide 100 would not need to be screwed in, but the drill guide 100 would not be secured to the bone plate as is the case for the threaded drill guide 100.

The distal end of the drill guide 100 also includes an opening 116 through which the drill bit passes in order to drill into the bone. The proximal end of the drill guide 100 includes a zero angle guide 104. The zero angle guide 104 is a cylinder with a zero angle opening 106. The zero angle opening 106 is aligned with the opening 116 in the distal end to provide a zero angle drilling option for the surgeon. The zero angle opening 106 is sized to correspond to the size of the drill bit used to drill the hole in the bone and to provide sufficient margin to allow the drill bit to operate but yet to keep the drill bit at a substantially zero degree angle.

Figure 1D:
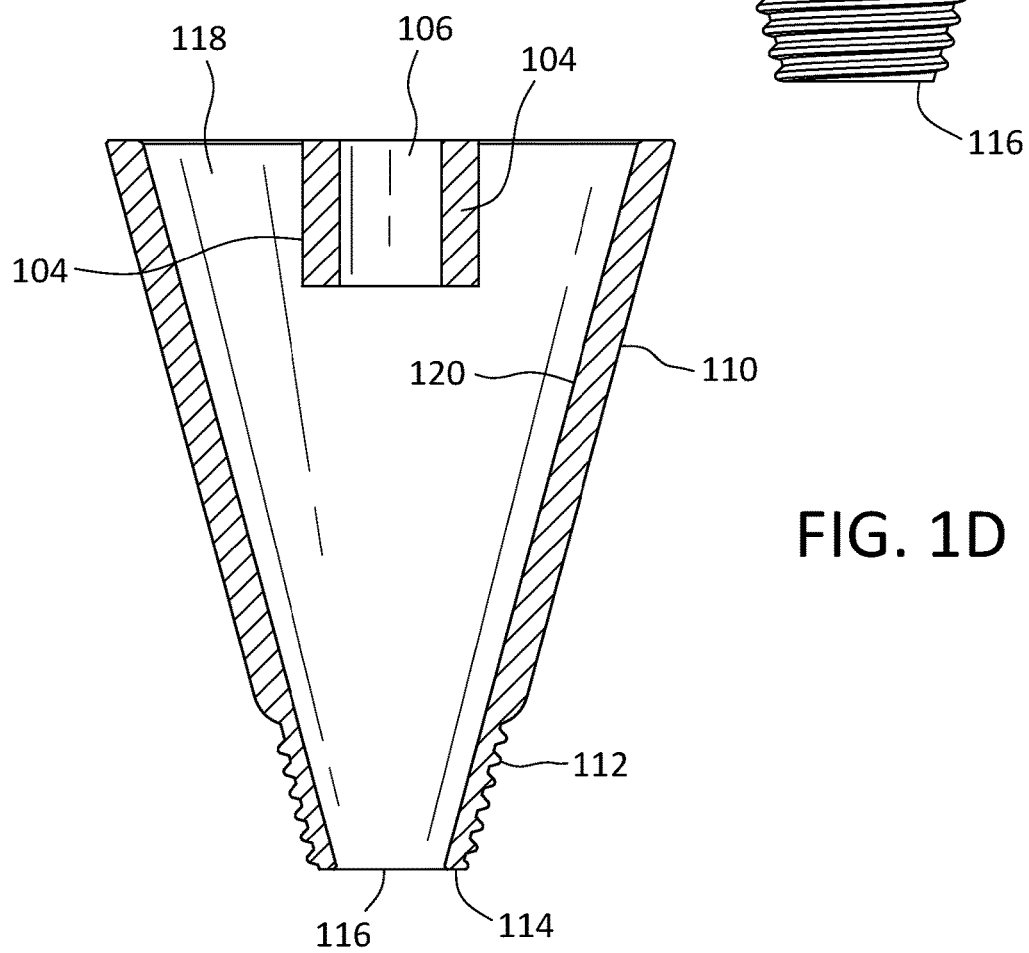

The zero angle guide 104 is held in place by supports 108. The zero angle guide 104 is adjacent the distal end of the drill guide 100 as shown in FIGS. 1A and 1D, but may also be located away from the distal end. The supports 108 are connected to both the zero angle guide 104 and the inner surface 120. In FIG. 1A three supports 108 are shown, but more or fewer supports are possible, including only one support 108. It is noted that the supports block angular areas where the drill bit may be placed, so choosing the number of supports leads to a balance between blocking a portion of available angles with increased strength in securing the zero angle guide 104 in place. Further, the supports 108 are as thin as possible to minimize blocking. A solution during use to avoid the supports 108 is to rotate the drill guide a bit so that the desired angle is not blocked. The opening between the supports 108 define VA drilling areas 118 that the surgeon may use to drill a hole at a non-zero angle.

Figure 2:
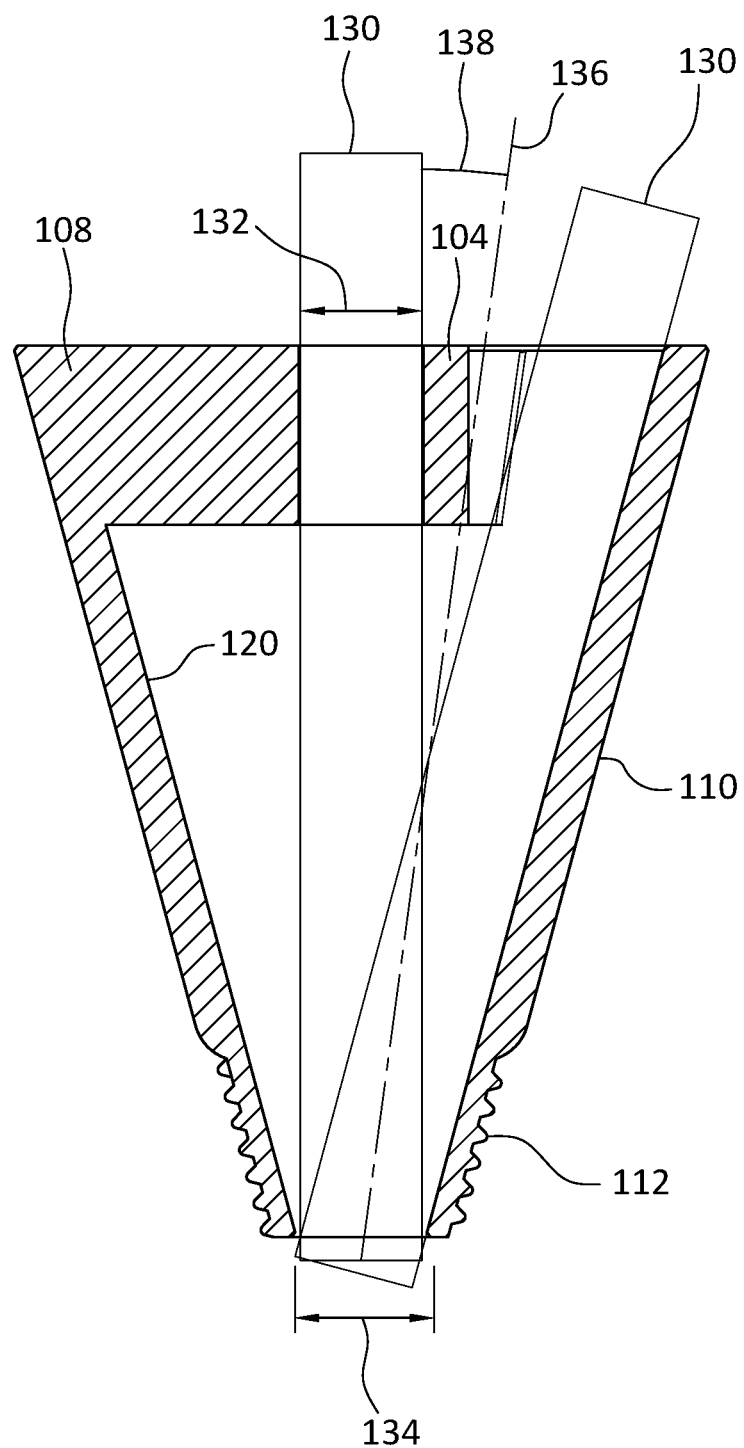
FIG. 2 illustrates a cross-sectional view of the drill guide 100 that shows angular limits on the drill bit when using the drill guide.
Figure 3A:
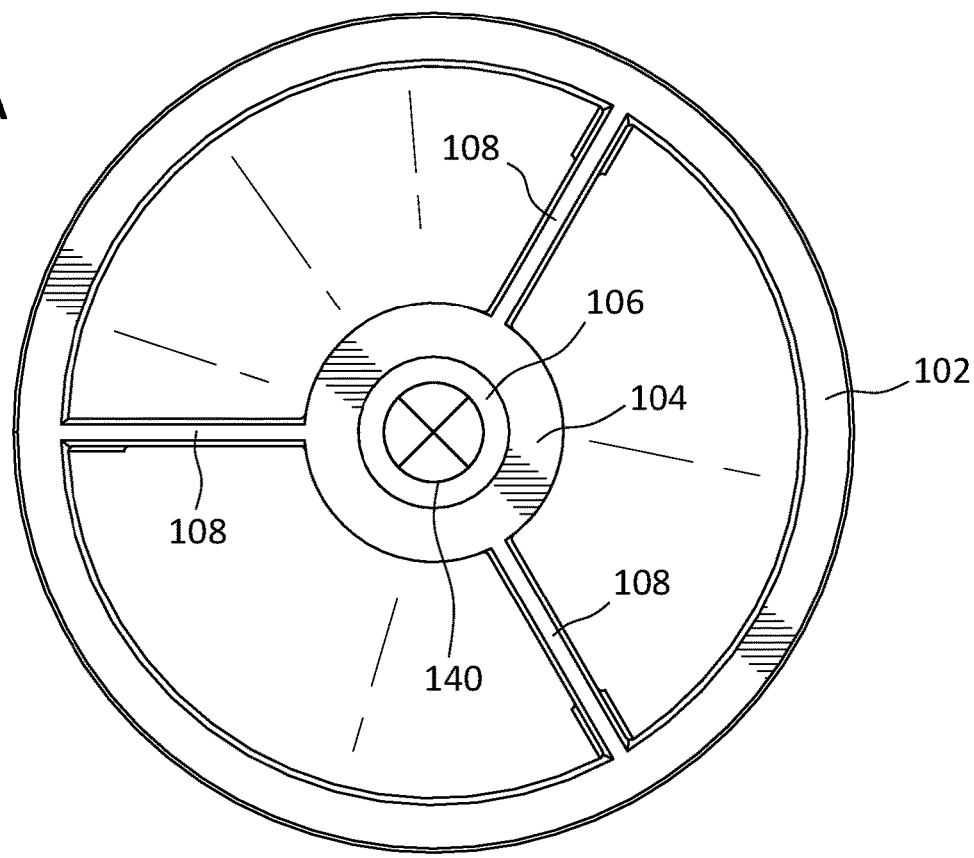
FIGS. 3A and 3B illustrate top views of the drill guide and multiple locations of a drill bit.
Figure 3B:
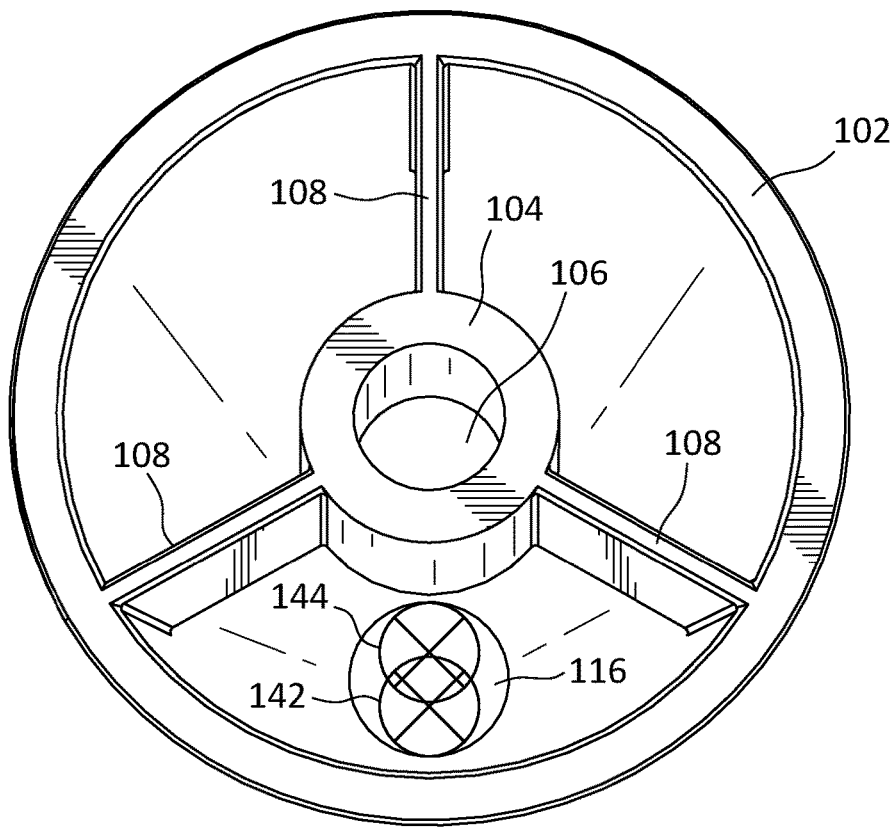

FIG. 2 illustrates a cross-sectional view of the drill guide 100 that shows angular limits on the drill bit when using the drill guide. FIGS. 3A and 3B illustrate top views of the drill guide and multiple locations of a drill bit. A drill bit 130 is shown in two different positions in FIG. 2. In the first position the drill bit 130 is inserted through the zero angle guide 104 and the opening 116. This is also shown by 140 in FIG. 3A. In the second position the drill bit 130 is inserted though the VA drilling area 118 at the maximum angle as defined by the inner surface 120. In FIG. 3B this may be shown by 142. In this specific example the maximum angle is 15°, but other maximum angles are possible based upon the shape of the drill guide 100. A line 136 shows the minimum angle possible because the zero angle guide 104 limits where the drill bit 130 may be placed. This position may correspond to item 142 in FIG. 3B. In this case a dead zone 138 from 0° to about 5° results. This dead zone may be reduced by either reducing the thickness and/or diameter of the zero angle guide 104 or by lengthening the drill guide 110 to allow the zero angle guide 104 to be farther away from the opening 116.

It is noted that the size 132 of the zero angle opening 106 may be smaller than the opening 134. As discussed above the size 132 of the zero angle opening 106 corresponds to the size of the drill bit. The size 134 of the opening 116 needs to be larger than the size of the drill bit 130 to accommodate when the drill bit is at the maximum angle.

The surgeon uses the drill guide 100 by engaging the drill guide 100 with the bone plate that may be held in the desired location. With the threaded drill guide 100 this will be done by screwing the drill guide 100 into a threaded hole in the bone plate. The surgeon then determines if a zero angle hole or VA hole is to be drilled in the bone. If a zero angle hole is to be drilled, the surgeon inserts the drill through the zero angle hole 106 and the opening 116 and drills the zero angle hole. If a VA hole is to be drilled, the surgeon places the drill through one of the VA drilling areas 118 and the opening 116 and drills the VA hole. As mentioned above, if the supports 108 block the desired drilling angle, the drill guide 100 may be rotated slightly along the threads to unblock the desired drilling angle.

Figure 4:
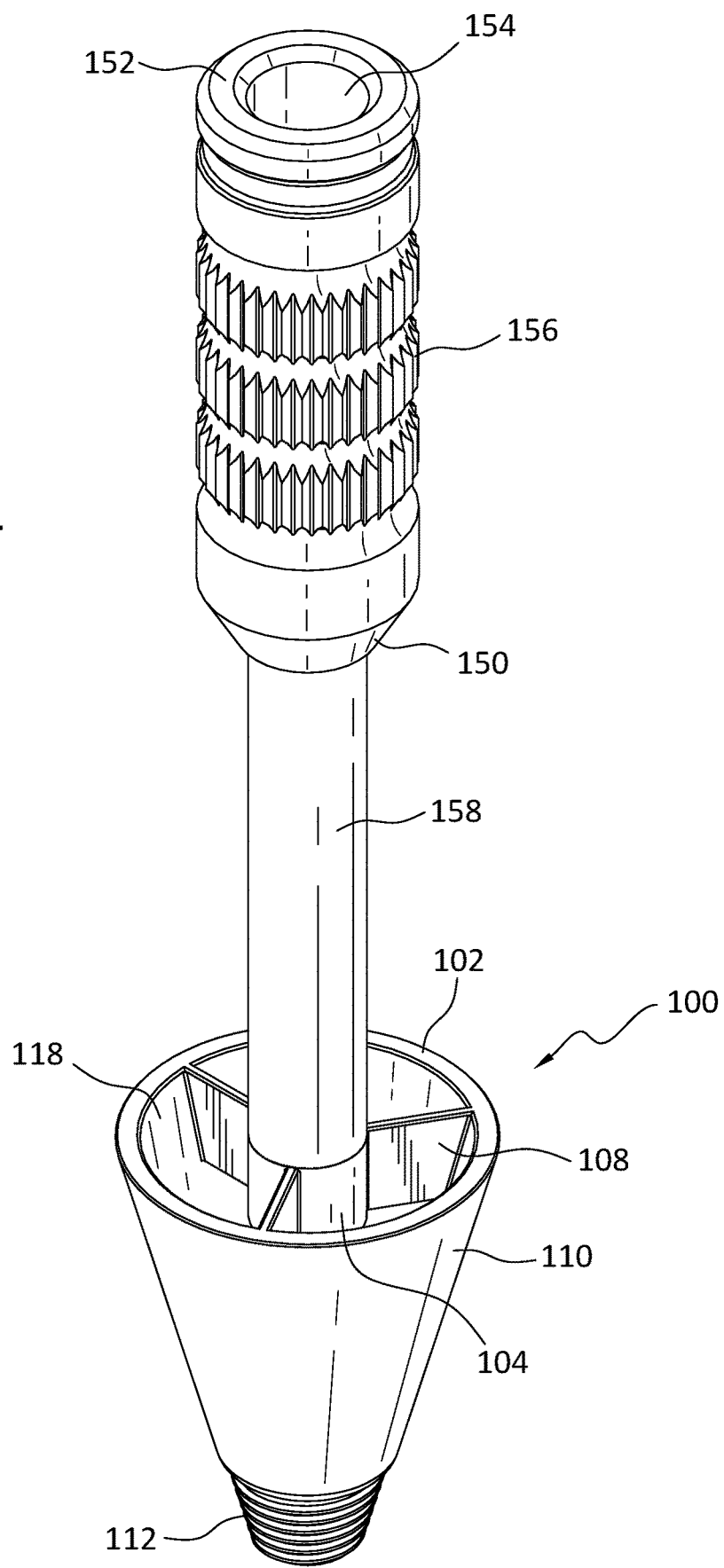
FIG. 4 illustrates an embodiment of the drill guide 110 with a handle.

FIG. 4 illustrates an embodiment of the drill guide 110 with a handle. The handle 150 extends from the zero angle guide 104 to a proximal end 152. The handle 150 may include a hollow shaft 158 and a grip 156. The hollow shaft 158 may extend from the zero angle guide 104 to the grip 156. The handle 150 may include a handle opening 154 that extends through both the grip 156 and hollow body 158 and joins with the zero angle opening 106. The handle opening 154 may accept the drill bit for drilling a zero angle hole. The grip 156 may have knurled areas that allow the surgeon to securely grip the drill guide 100. Other types of handles may be used with the drill guide as well. For example, a handle may be attached to the outer surface 110 and extend from the outer surface 110.

Figure 6B:
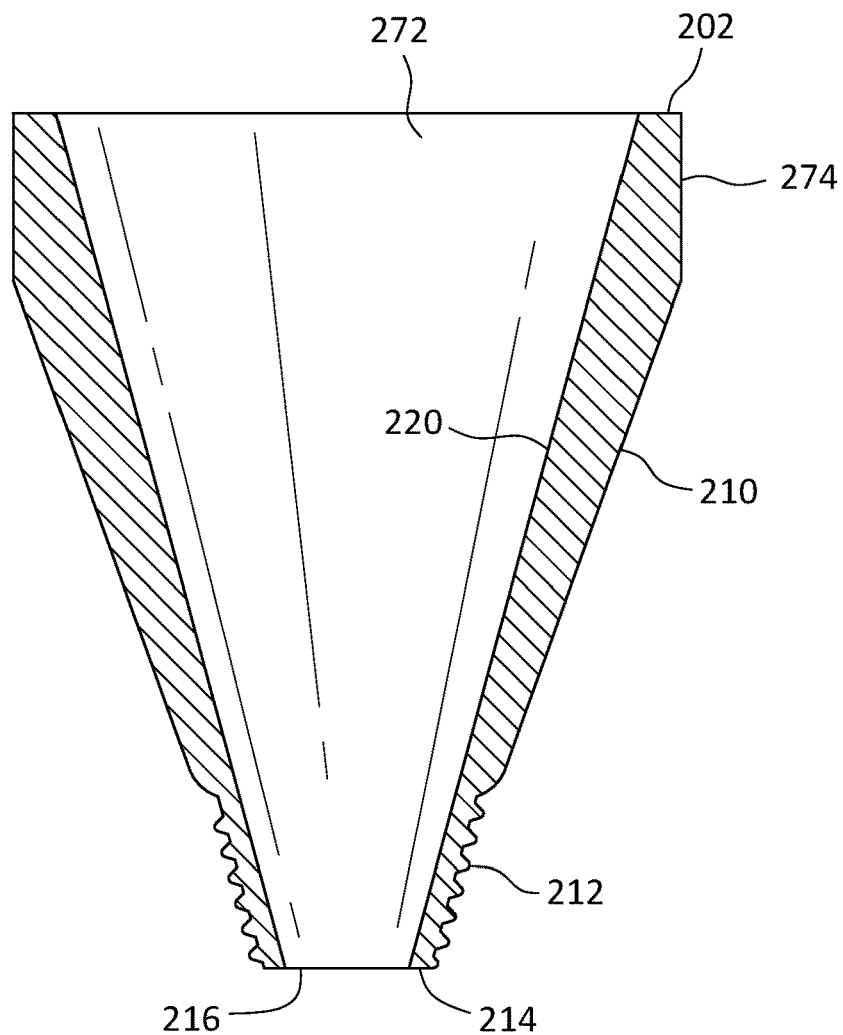

FIG. 5 illustrates another embodiment of a drill guide with a separate guide assembly. The drill guide 200 includes a guide assembly 250 and guide body 270. FIGS. 6A and 6B illustrate perspective and cross-sectional views, respectively, of the guide body 270. The guide body 270 has a substantially frustoconical shape as shown by the inner wall 220, outer wall 210, and outer lip 274. The guide body 270 includes a proximal end with a proximal edge 202 and a distal end with a distal edge 214. The distal end is configured to engage a screw hole on the bone plate. This may be facilitated by a thread 212 on the outer surface 210. The thread 212 may engage threads in the bone plate hole. This will ensure that the drill guide 210 is securely engaged with the bone plate while screw holes are drilled in the bone. The thread 212 also helps to ensure that the guide body 270 is substantially aligned with the axis of the bone plate screw hole to provide the surgeon confidence in the angle of the hole being drilled into the bone. In other embodiments the distal end of the guide body 270 may be shaped to fit securely in the bone plate screw hole in a specific desired orientation because of the complementary mating surfaces. Such an approach would save time because the guide body 270 would not need to be screwed in, but the guide body 270 would not be secured to the bone plate as is the case for the threaded guide body 270.

The distal end of the guide body 270 also includes an opening 216 through which the drill bit passes in order to drill into the bone. The size of the opening 216 needs to be larger than the size of the drill bit to accommodate when the drill bit is at the maximum angle. The proximal end of the guide body 270 includes an opening 272 through which the drill bit also passes in order to drill into the bone.

When the surgeon would like to drill a hole in the bone with a variable angle, the guide body 270 will be used by itself. The inner wall 220 defines the conical angular limit for such holes, which in this example is approximately 15°. In this embodiment, there is no dead zone as the complete angular region within the conical angular limits is available. When the surgeon wants to drill a zero angle hole, then the guide assembly 250 may be placed on the guide body 270. The guide assembly 250 engages the outer lip 274 so that the guide assembly 250 is precisely and securely attached to the guide body 270. The outer lip 274 is a circular surface on the outside of the proximal end of the guide assembly 250 that is substantially aligned with a central axis of the guide body 270.

Figure 7A:
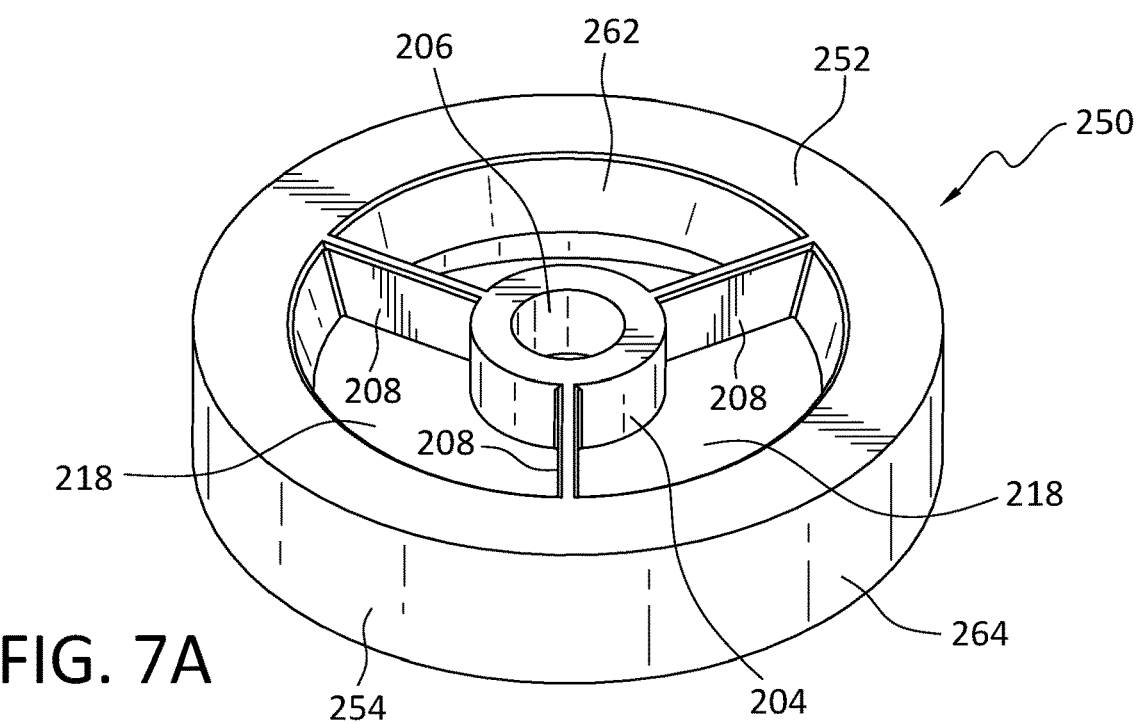
FIGS. 7A-7C illustrate top perspective, bottom perspective, and cross-sectional views, respectively, of the guide assembly.
Figure 7B:
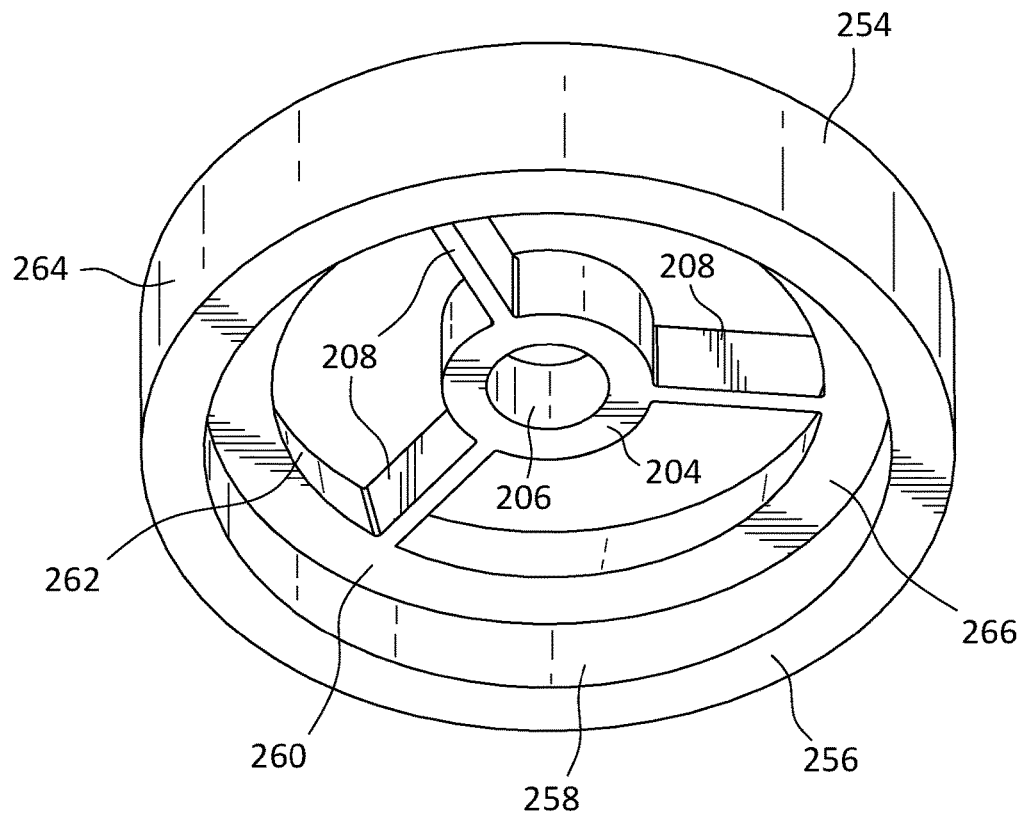
Figure 7C:
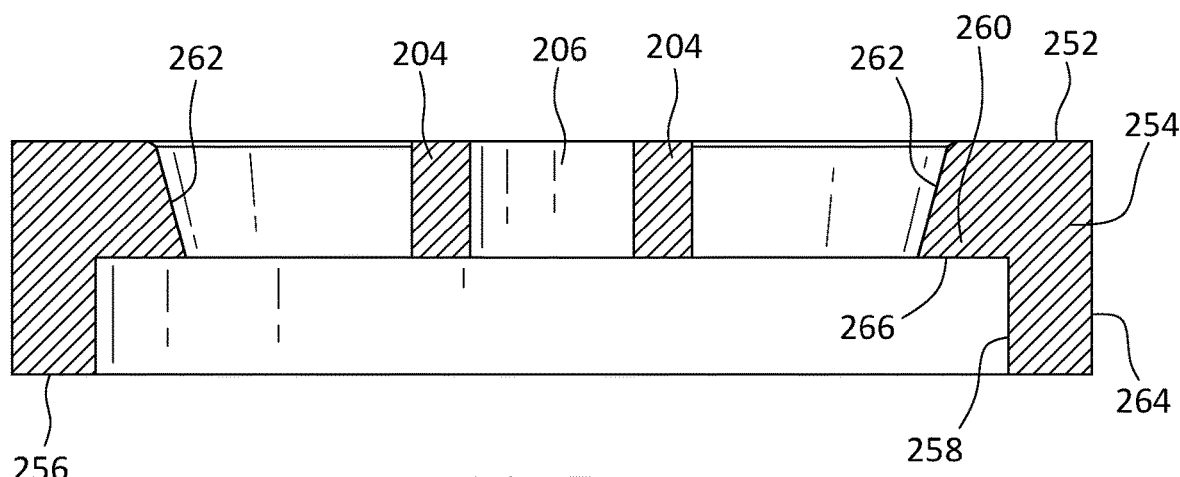

FIGS. 7A-7C illustrate top perspective, bottom perspective, and cross-sectional views, respectively, of the guide assembly 250. The guide assembly 250 includes a circular body 254. The circular body 254 includes an outer surface 264, and inner surface 258, an upper surface 252, and a lower surface 256. The circular body 254 may also include a ledge 260 that has a ledge lower surface 266 and a ledge inner surface 262.

The guide assembly 250 includes a zero angle guide 204. The zero angle guide 204 is a cylinder with a zero angle opening 206. The zero angle opening 206 is aligned with the opening 216 in the guide assembly 250 to provide a zero angle drilling option for the surgeon. The zero angle opening 206 is sized to correspond to the size of the drill bit used to drill the hole in the bone and to provide sufficient margin to allow the drill bit to operate but yet to keep the drill bit at a substantially zero degree angle.

The zero angle guide 204 is held in place by supports 208. The supports 208 are connected to both the zero angle guide 204 and the circular body 254. In FIGS. 7A and 7B three supports 208 are shown, but more or fewer supports are possible, including only one support 208. The supports 208 along with the circular ring 254 define VA openings 218. These VA openings 218 may also be used to drill VA holes with the guide assembly 250 in place, but with the same angular limitations as described for the drill guide 100.

When the guide assembly 250 is placed over the guide body 270, the inner surface 258 of the guide assembly 250 engages the outer lip 274 of the guide body 270. Further, the ledge lower surface 266 of the guide assembly 250 may engage the proximal edge 202 of the guide body 270. These various engagement surfaces align the zero angle hole 206 with the opening 216 of the guide body 270 to allow the surgeon to drill a zero angle hole in the bone.

FIG. 7C illustrates the geometry of the ledge inner surface 262. The ledge inner surface 262 has an angle that corresponds to the inner surface 220 of the guide body 270 so that the ledge inner surface 262 and the inner surface 220 are aligned to define the angular limit that may be used for drilling holes in the bone.

In other embodiments, the ledge lower surface 266 may not be present, but instead the lower edge of the ledge inner surface 220 meets the upper edges of the inner surface 258.

In this case the upper edge 202 of the guide body 270 will engage the supports 208 of the guide assembly 250 when the guide assembly 250 is placed on the guide body 270.

In other embodiment of the drill guide 200, a handle may be attached to the outer surface of the guide body 270 and extend from the drill body 270.

The surgeon uses the drill guide 200 by engaging the guide body 270 with the bone plate that may be held in the desired location. With the threaded guide body 270 this will be done by screwing the guide body 270 into a threaded hole in the bone plate. The surgeon then determines if a zero angle hole or VA hole is to be drilled in the bone. If a VA hole is to be drilled, the surgeon places the drill through the opening 272 and the opening 216 at the desired variable angle and drills the VA hole. If a zero angle hole is to be drilled, the surgeon puts the guide assembly 250 on the guide body 270 and then inserts the drill through the zero angle hole 206 and the opening 216 and drills the zero angle hole. The guide assembly 250 may be rotated on the guide assembly 270 to ensure that none of the supports 208 block the desired drilling angle.

FIGS. 8A and 8B illustrate another embodiment of a drill guide. The drill guide 300 includes a VA guiding cone 310 attached to a handle 330. The VA guiding cone 310 has a frustoconical shape. The VA guiding cone 310 allows for the drilling of holes at angles with a conical angular limit based upon the shape of the VA guiding cone 310 as is the case for the drill guides described above. The VA guiding cone 310 may include a distal edge 314 and a proximal edge 302. The VA guiding cone 310 may also include threads 312 where the threads 312 engage threads in the bone plate in the same manner as described above. In other embodiments the distal end of the VA guiding cone 310 may be shaped to fit securely in the bone plate screw hole in a specific desired orientation because of the complementary mating surfaces The drill guide 300 also includes a sliding bar 308. The sliding bar 308 slides along a sliding groove 332. The sliding groove 332 may also include an engagement mechanism that locks the slide in an upper position. The sliding groove 332 allows the sliding bar 308 to be slid downward so that a distal end of the sliding bar 308 enters the inside of the VA drilling cone 310. The VA drilling cone 310 may have an aperture in the side adjacent to the handle that allows the sliding bar 308 to enter the VA drilling cone 310. A zero angle hole 306 is at the distal end of the sliding bar 308. The zero angle hole 306 has an angle that is aligned with a central axis of the VA drilling cone 310 and with the opening 314. The distal end of the sliding bar 308 engages an inner surface 320 of the VA drilling cone 310 so that the zero angle hole 306 is aligned with the opening 314. With the sliding bar 308 in this position, the surgeon may drill a zero angle hole in the bone. A further engagement mechanism may lock the sliding bar 308 in the downward position to facilitate zero angle drilling.

In other embodiments, the sliding bar 308 may be on the underside of the handle 330 instead of on top of the handle 330 as shown in FIGS. 8A and 8B. Also, the sliding bar 308 may be substantially enclosed in the handle, with a tab extending out of the handle in a slot to allow the sliding bar 308 to be moved using the tab. In either of these embodiments the aperture in the VA guiding cone 310 is adjusted to accommodate the sliding bar 308 entering the VA guiding cone 310.

The surgeon uses the drill guide 300 by engaging the VA guiding cone with the bone plate. The surgeon can then position the sliding bar in a up or down position to be able to drill either a VA hole or zero angle hole, respectively.

The drill guides may be made of any surgical grade material, such as stainless steel, titanium, other metals, plastic, etc. The drill guides may be manufactured using milling, molding, or additive manufacturing methods. The dimensions of the drill guide are selected to provide a desired conical angular limit for drilling holes in the bone. Further, for the drill guide 100, the length of the drill guide and the dimensions of the zero angle guide 104 will selected to define the limits of the dead zone of drilling angles.

While each of the embodiments are described above in terms of their structural arrangements, it should be appreciated that the invention also covers the associated methods of using the embodiments described above.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications and combinations of the various embodiments can be affected while remaining within the spirit and scope of the invention. Accordingly, the foregoing disclosure, description, and figures are for illustrative purposes only and do not in any way limit the invention, which is defined only by the claims.

What is claimed is:

1. A drill guide, comprising:
frustoconical body with a first opening at a narrower distal end and second opening at a wider the proximal end;
a first support with a first end connected to the frustoconical body and a second end;
a zero angle guide with an opening aligned with the first opening and wherein the zero angle guide is connected to the second end of the first support.

2. The drill guide of claim 1, wherein the frustoconical body includes threads at the distal end configured to engage a screw hole in a bone plate.

3. The drill guide of claim 1, wherein the distal end of frustoconical body has a shape configured to engage a screw hole in a bone plate, wherein the shape of the distal end is complementary to the shape of the screw hole.

4. The drill guide of claim 1, further comprising a second support with a first end connected to the frustoconical body and a second end connected to the zero angle guide.

5. The drill guide of claim 1, wherein the zero angle guide is adjacent the distal end of the frustoconical body.

6. The drill guide of claim 1, further comprising a handle.

7. The drill guide of claim 6, wherein the handle is connected to and extends from the zero angle guide along a central axis of the zero angle hole and wherein the handle has a central opening aligned with the zero angle guide opening.

8. The drill guide of claim 6, wherein the handle is connected to and extends from the frustoconical body.

* * * * *